(12) United States Patent
Scordamaglia-Crockett et al.

(10) Patent No.: US 6,458,372 B1
(45) Date of Patent: Oct. 1, 2002

(54) GEL POWDER COMPOSITION

(75) Inventors: Barbara A. Scordamaglia-Crockett, Greenlawn; Timothy W. Hackford, Stewart Manor, both of NY (US)

(73) Assignee: Color Access, Inc., Melville, NY (US)

( * ) Notice: Subject to any disclaimer, the term of this patent is extended or adjusted under 35 U.S.C. 154(b) by 0 days.

(21) Appl. No.: 09/554,430

(22) PCT Filed: Mar. 8, 2000

(86) PCT No.: PCT/US00/05927

§ 371 (c)(1),
(2), (4) Date: Jan. 4, 2001

(87) PCT Pub. No.: WO00/56272

PCT Pub. Date: Sep. 28, 2000

(51) Int. Cl.$^7$ .................................................. A61K 7/00
(52) U.S. Cl. ...................... 424/401; 424/69; 424/78.02; 424/489
(58) Field of Search ....................... 424/401, 69, 78.02, 424/489

(56) References Cited

U.S. PATENT DOCUMENTS

| | | | | |
|---|---|---|---|---|
| 4,892,726 A | | 1/1990 | Yonekura | ...................... 424/63 |
| 5,658,577 A | * | 8/1997 | Fowler et al. | ............... 424/401 |

* cited by examiner

Primary Examiner—Jose' G. Dees
Assistant Examiner—Konata M George
(74) Attorney, Agent, or Firm—Karen A. Lowney, Esq.

(57) ABSTRACT

The invention relates to liquid powder compositions that are applied as liquid and dry to a powder on the skin. The compositions comprise a cosmetically acceptable liquid base and a powder component comprising at least one type of cosmetically acceptable microparticle.

27 Claims, No Drawings

GEL POWDER COMPOSITION

This application is a 371 of PCT/US00/05927 filed Mar. 8, 2000; which claims benefit of U.S. application Ser. No. 09/273,087 filed Mar. 19, 1999 now abandoned.

FIELD OF THE INVENTION

The invention relates to cosmetic compositions. More specifically, the invention relates to gel powder compositions with improved feel on application to skin.

BACKGROUND OF THE INVENTION

Liquid powder compositions have become very popular in recent years for a number of reasons. Such compositions have an advantage over the traditional dusting powders in the mode of delivery is more precise; with a standard dusting powder, the user was forced to sprinkle the product over the areas where powder application was desired. Because of the light weight and particulate nature of powders generally, however, precise and limited application of the powder to the body was difficult. With liquid powders, however, the user simply smoothes the liquid product on the part of the body on which powder application is desired, and after a short time, the liquid evaporates, leaving behind the powder only where it is needed. Generally speaking, liquid powders are intended to be initially refreshing and smoothing to the skin, with the liquid base eventually transforming to a silky powder on the skin. Unlike other cosmetics that utilize powder components, for example mica, or other fillers used in color cosmetics, the user is intended to feel the powder on the skin, and to that end the powder components tend to be of a larger particle size than in other powder-containing cosmetics.

Liquid powders come in a variety of forms. All have in common the presence of a particulate powdery material combined with at least one volatile component. For example, U.S. Pat. Nos. 5,338,535 and 5,626,856 disclose non-aqueous liquid powders containing a volatile cyclomethicone combined with particulate carbohydrates such as cornstarch or tapioca. Non-aqueous compositions, however, can have a heavy or greasy feel when being applied initially, and thus may be less desirable for individuals with oily skin. Aqueous or alcoholic powder products are also known. These provide the advantage of a non-oily base, and thus can be more refreshing and cooling to apply and wear than oil-based, non-aqueous products. In such non-oily products, alcohol, water, or more typically, alcohol combined with water provide the volatile component, and the powder utilized is again primarily a starch such as tapioca or cornstarch.

In the majority of liquid powders, the particulate carbohydrates are the traditional powder components. This is primarily due to the cost of the materials, which is fairly low. Although effective in providing a powdery feel, however, these components can often leave a gritty uneven feeling on the skin when the volatile evaporates off. There thus continues to be a need for a liquid powder that provides the desirable cool feeling upon application and dry down, but which leaves a silky, smooth feeling on the skin when only the powder component remains.

SUMMARY OF THE INVENTION

The present invention relates to an liquid gel powder composition comprising a liquid carrier, and a powder component comprising at least one type of cosmetically acceptable spherical microparticle. In a preferred embodiment, the spherical microparticle is a silicone resin, a polyurethane particle, or a combination of both. The microparticles can form all or a part of the powder component of the composition.

DETAILED DESCRIPTION OF THE INVENTION

The composition of the invention provides a cooling liquid powder composition that leaves a very smooth, powdery but non-gritty feeling on the skin when the volatile portion has evaporated off. It has been unexpectedly discovered that incorporation of spherical microparticles as all or a portion of the powder phase of an otherwise standard aqueous liquid powder composition confers a substantially different feel to the final product on the skin. Unlike the previously employed particulate carbohydrates, the particles of the invention are regularly spherical, and have a relatively uniform particle size distribution. In a preferred embodiment, the average particle diameter of the microspheres ranges from about 1–20$\mu$. Particles of this type can be of a variety of chemical compositions, for example, nylon, silica, silicone resin, polyethylene, polyurethane, and acrylate or methacrylate polymers or copolymers. Particularly preferred among these microspheres are polyurethane and silicone resin microspheres. Examples of commercially available resins of these types are BPD-500, a polyurethane (HDI/trimethylyol hexyl lactone) microsphere, and Tospearl silicone resin (polymethylsilsesquioxane) microspheres, both available from Kobo Products, Inc., South Plainfield, N.J. Particularly preferred of the Tospearl microspheres is Tospearl 145, having an average particle diameter of about 4.5$\mu$. Similar microspheres are also available from Presperse (Piscataway, N.J.).

The powder component of the composition comprises at least one type of spherical microparticle, but may also comprise a combination of microspheres. Overall, the powder component can comprise from about 1–30% by weight of the total composition, more preferably in the range of from 5–20%. The microspheres can be all or portion of the powder component; in other words, the spherical microparticles can be combined with other powder components. It has been unexpectedly discovered that a very desirable, soft, silky product can be obtained by the combination of the microspheres with a bulking agent or powder component. Examples of useful bulking agents are particulate carbohydrates e.g., starches, such as tapioca starch, corn starch, rice starch, potato starch, or wheat starch. Other useful bulking agents, particularly for non-aqueous products are amylopectin, agar, cellulose or a cellulose ether, glycogen, algin or carrageenan. Silica, nylon, polyethylene, polypropylene, mica, or talc could also be used. Starches are particularly preferred for aqueous gel powders. Particularly surprising is that even a relatively small proportion of microspheres can substantially improve the feel of the final product. Preferably, the starch and microspheres are present in a ratio of 5:1 to 1:5 (starch to microspheres), more preferably 3:1 to 1.5:1. In fact, although a product containing all microspheres as powder component exhibits a silky powdery feel superior to that of an identical product containing all starch, a product containing a mixture of microspheres and starch exhibits an even better after-feel, and initially goes on more smoothly, with less tackiness, than either of the other products. In addition, the combination of starch and microspheres permits the formulation of an enhanced product with relatively little increase in expense over the product containing only starch.

The carrier can be any cosmetically acceptable liquid carrier, but is preferably one which has a volatile component that evaporates off the skin fairly rapidly. Particularly preferred is a gel base, which permits the suspension the powder and microparticle components. Preferably, the base is aqueous, and in a particularly preferred embodiment, the aqueous base is an aqueous gel. The gelling agent can be any which is appropriate for gelling an aqueous base, and includes, but is not limited to, carbomer, hydroxypropyl methylcellulose, hydroxyethylcellulose, hydroxy propyl guar, hydroxypropyl cellulose, or potato starch modified. Particularly preferred is an acrylates/C10–C30 alkyl acrylates crosspolymer, commercially available under the tradename Pemulen TR-2 from (B. F. Goodrich Specialty Chemicals, Cleveland, Ohio).

Although less preferred, the base may also be oily, or contain an oil component. A preferred oil base comprises a volatile oil, such as volatile cyclic and linear silicones, for example, cyclomethicone; or straight or branched chain hydrocarbons having from 8–20 carbon atoms, such as decane, dodecane, tridecane, tetradecane, and C8–20 isoparaffins. A preferred volatile oil is cyclomethicone. Useful oil gellants include, but are not limited to, organopolysiloxane elastomers, ethylene/methacrylic acid copolymer, ethylene/acrylic acid copolymer, or polyethylene.

Generally speaking, the liquid base component will constitute from about 10 to about 90%, preferably about 20 to about 60%, more preferably from about 30–50%, by weight of the total composition. The amount of gellant will vary depending upon the identity of the gellant, and the desired texture of the final product, but generally will be in the range of from about 0.1 to about 5% of the total composition.

There may be other optional components forming part of the composition. Since the liquid powder composition can be used for a variety of purposes, and not just as a body powder, it may be desirable to add additional components depending on the intended end use. In some cases, the desired components may not necessarily be soluble in an aqueous base. In such a case, it will be desirable to add an alcohol component to assist in solubilizing such components. The preferred alcohol component is a short chain, i.e., C1–C4 monohydric alcohol, such as methanol, ethanol or isopropanol. The alcohol also acts as a volatile to facilitate the rapid drying of the product. The alcohol component, if used will normally be present in an amount of from about 20–70% by weight.

In a particularly preferred embodiment, the composition is used as a body powder, preferably a fragranced body powder. In such a composition, fragrance will normally be added in an amount of from about 0.1–6% by weight of the composition. Such compositions can also contain standard cosmetic ingredients, such as colorants, preservatives, emulsifiers, skin conditioners, emollients, and the like. In addition to this embodiment, however, as noted above, the liquid powder composition can also be used for purposes other than a body powder. For example, it may be used as a delivery system to provide both cosmetic and pharmaceutical actives to the skin. Thus, in addition to the essential components of the invention, the composition can also comprise one or more active components. Examples of such active agents which may form part of the composition include, but are not limited to, those that improve or eradicate age spots, keratoses and wrinkles, analgesics, anesthetics, anti-acne agents, antibacterials, antiyeast agents, antifungal agents, antiviral agents, antidandruff agents, antidermatitis agents, antipruritic agents, antiemetics, antimotion sickness agents, anti-inflammatory agents, antihyperkeratolytic agents, anti-dry skin agents, antiperspirants, antipsoriatic agents, antiseborrheic agents, antiaging agents, antiwrinkle agents, antiasthmatic agents and bronchodilators, sunscreen agents, antihistamine agents, skin lightening agents, depigmenting agents, wound-healing agents, vitamins, corticosteroids, self-tanning agents, antioxidants, free-radical scavengers, or hormones. More specific examples of useful active agents include retinoids, topical cardiovascular agents, clotriiazole, ketoconazole, miconozole, griseofuilvin, hydroxyzine, diphenhydramine, pramoxine, lidocaine, procaine, mepivacaine, monobenzone, erythromycin, tetracycline, clindamycin, meclocyline, hydroquinone, minocycline, naproxen, ibuprofen, theophylline, cromolyn, albuterol, retinol, retinoic acid, 13-cis retinoic acid, hydrocortisone, hydrocortisone 21-acetate, hydrocortisone 17-valerate, hydrocortisone 17-butyrate, betamethasone valerate, betamethasone diprorionate, triamcinolone acetonide, fluocinonide, clobetasol, proprionate, benzoyl peroxide, crotariton, propranolol, promethazine, vitamin A palmitate, vitamin E acetate, DHEA and derivatives thereof, alpha- or beta-hydroxy acids, and mixtures thereof. The amount of active agent to be used in any given formulation is readily determined in accordance with its usual dosage.

The invention is further illustrated by the following non-limiting examples:

EXAMPLES

Example I.

The following formula represents a fragranced body powder prepared according to the invention:

| Material | Weight Percent |
| --- | --- |
| Phase I | |
| water | QS |
| benzophenone-4 | 0.30 |
| Phase II | |
| acrylates/C10–C30 alkyl acrylate crosspolymer | 0.45 |
| Phase III | |
| octyl methoxycinnamate | 0.10 |
| isostearyl neopentanoate | 1.00 |
| tocopheryl acetate | 0.05 |
| Phase IV | |
| tapioca starch | 12.00 |
| polymethylsilsesquioxane | 4.00 |
| HDI/trimethylol hexylactone crosspolymer | 3.00 |
| Phase V | |
| fragrance | 3.00 |
| denatured alcohol | 30.00 |
| Phase VI | |
| phenoxyethanol | 0.70 |
| stearyl heptanoate | 3.00 |
| dimethicone copolyol | 0.75 |
| Phase VII | |
| cyclomethicone/dimethicone copolyol | 1.25 |

The materials of Phase III are premixed under propeller agitation while heating to 60° C., and mixed until all components are dissolved. Phase II is sprinkled into Phase III materials until uniformly dispersed. In a separate kettle, Phase I materials are mixed under propeller agitation until all solids are dissolved. The combined Phases II and III are added to Phase I, and the gellant allowed to hydrate for 30 minutes. A premix of phase VI materials is made, and then added to the materials in the kettle while propeller mixing and heating to 50° C., then mixing until all solids are dissolved. Phase V materials are separately mixed until uniform. After a 30 minute mix, the Phase IV powders are sprinkled into the main kettle and mixed until all powders are uniformly dispersed. The Phase V materials are then added to the main kettle with propeller mixing. Finally, Phase VII is added under side-swipe agitation.

Example II

Three liquid powder products are compared to determine consumer's perceptions of some key aesthetic characteristics. The three products compared were: (T&S) a product containing both spherical powders and tapioca, as described in Example I; (T)a product containing only tapioca; and (S)a product containing only spherical powders. Each product is tested with a total of 52 females ages 18–60, with normal or normal/oily body skin, and who are regular users of a body lotion or body powder. The panelists are instructed to smooth the product all over the body at least once a day and not to use any other body lotions or body powders during the test period. Each product is tested for a period of two weeks, after which a self-administered questionnaire is answered by the panelist.

With respect to the characteristic of product texture, both spherical powder containing products are found by the panelists to be more soft, smooth and silky than the product containing only tapioca. The product containing both tapioca and spherical powders performs best of all the tested products in this category(extremely/very soft/smooth/silky: T&S87% vs. T69% vs. S81%). Similarly, both spherical powder-containing products received higher ratings on the measures of positive purchase intent(definitely/probably would buy:T&S73% vs. T56% vs. S65%) and overall ratings (excellent/very good:T&S:73% vs. T54% vs. S65%), with the tapioca and spherical powder product receiving the highest ratings in all these categories.

What we claim is:

1. A liquid powder composition comprising a cosmetically acceptable liquid base, a powder component comprising at least one type of cosmetically acceptable spherical microparticle and a volatile component, wherein the composition is liquid when applied to the skin, and dries to a powder on the skin after application.

2. The composition of claim 1 in which the base is a gel.

3. The composition of claim 1 in which the microparticles have an average particle size diameter of about 1 to about 20μ, and are selected from the group consisting of nylon, silica, silicone resin, polyethylene, polyurethane, and acrylate or methacrylate polymers or copolymer microparticles.

4. The composition of claim 3 in which the powder component comprises polyurethane microparticles.

5. The composition of claim 3 in which the powder component comprises silicone resin microparticles.

6. The composition of claim 1 in which the powder component comprises both silicone resin microspheres and polyurethane microparticles.

7. The composition of claim 1 in which the powder component comprises a starch.

8. The composition of claim 7 in which the starch is tapioca or corn starch.

9. An aqueous liquid powder gel comprising an aqueous base and a gelling agent, a volatile component, and a powder component comprising at least one cosmetically acceptable microparticle, wherein the gel is liquid when applied to the skin, and dries to a powder on the skin after application.

10. The gel of claim 9 comrising a microparticle selected from the group consisting of mylon, silica, silicone resin, polyethlene, polyurethane, and acrylate or methacrylate polymers or copolymers.

11. The gel of claim 10 in which the average particle size diameter of the microparticle is about 1 to about 20μ.

12. The gel of claim 10 in which the powder component comprises polyurethane microparticles.

13. The gel of claim 10 in which the powder component comprises silicone resin microparticles.

14. The gel of claim 10 in which the powder component comprises both polyurethane and silicone resin microparticles, each having an average particle size diameter of about 1 to about 20μ.

15. The gel of claim 10 in which the powder component also comprises a starch.

16. The gel of claim 9 which comprises a gelling agent selected from the group consisting of carbomer, hydroxypropyl methylcellulose, hydroxyethylcellulose, hydroxy propyl guar, hydroxypropyl cellulose, potato starch modified, and acrylates/C10–C30 alkyl acrylates crosspolymer.

17. The gel of claim 9 which comprises an aqueous base and a gelling agent, and a powder component comprising spherical microparticles combined with a starch.

18. The gel of claim 17 which comprises an aqueous base, a gelling agent selected from the group consisting of carbomer, hydroxypropyl methylcellulose, hydroxyethylcellulose, hydroxy propyl guar, hydroxypropyl cellulose, potato starch modified, and acrylates/C10–C30 alkyl acrylates crosspolymer; microparticles having an average particle size diameter of about 1 to about 20μ and being selected from the group consisting of nylon, silica, silicone resin, polyethylene, polyurethane, and acrylate or methacrylate polymers or copolymer microparticles; and a starch selected from the group consisting of tapioca starch, corn starch, rice starch, potato starch, and wheat starch.

19. The gel of claim 18 which comprises an aqueous base; an acrylates/C10–C30 alkyl acrylates crosspolymer; and a powder component comprising microparticles selected from the group consisting of polyurethane microparticles, silicone resin microparticles and combinations thereof combined with a tapioca or corn starch.

20. The gel of claim 18 which comprises from about 10–90% of an aqueous base; from about 0.1 to about 5% of an acrylates/C10–C30 alkyl acrylates crosspolymer; and from about 1 to about 30% of a powder component, the powder component comprising microparticles selected from the group consisting of polyurethane microparticles, silicone resin microparticles and a combination thereof combined with a starch.

21. The gel of claim 20 in which the powder component comprises about 0.1–5% polyurethane microparticles, about 0.1–5% silicone resin microparticles, and about 1–20% tapioca starch.

22. The gel of claim 20 which also comprises about 20 to about 70% of a short-chain monohydric alcohol component.

23. An aqueous liquid powder gel comprising an aqueous base and a gelling agent, a volatile component, and a powder component comprising at least one cosmetically acceptable microparticle and at least one starch, wherein the gel is liquid when applied to the skin, and dries to a powder on the skin after application.

24. The gel of claim 23 in which the powder component comprises at least two spherical microparticles.

25. The gel of claim 24 in which the powder component comprises spherical microparticles selected from the group consisting of polyurethane microparticles, silicone resin microparticles and a combination thereof, and a starch selected from the group consisting of tapioca and cornstarch.

26. The gel of claim 25 in which the gellant is selected from the group consisting of carboner, hydroxypropyl methylcellulose, hydroxyethylcellulose, hydroxy propyl guar, hydroxypropyl cellulose, potato starch modified, and acrylates/C10–C30 alkyl acrylates crosspolymer.

27. The gel of claim 26 which has a short-chain monohydric alcohol component.

* * * * *